United States Patent [19]

Hesse

[11] Patent Number: Plant 6,835

[45] Date of Patent: Jun. 6, 1989

[54] CHRYSANTHEMUM PLANT NAMED CARNIVAL

[75] Inventor: Peter S. Hesse, Bradenton, Fla.

[73] Assignee: Ball Seed Company, W. Chicago, Ill.

[21] Appl. No.: 150,063

[22] Filed: Jan. 29, 1988

[51] Int. Cl.[4] ..... A01H 5/00

[52] U.S. Cl. ..... Plt./74

[58] Field of Search ..... Plt./74

*Primary Examiner*—Robert E. Bagwill

*Attorney, Agent, or Firm*—Foley & Lardner, Schwartz, Jeffery, Schwaab, Mack, Blumenthal & Evans

[57] ABSTRACT

A Chrysanthemum plant named Carnival having bright yellow quilled and spoon tipped daisy flowers; strong, vigorous and upright growth habit, excellent keeping quality, high floriferousness, nine week response, and an ability to perform well year around in pot mum programs.

1 Drawing Sheet

The present invention comprises a new and distinct cultivar of *Dendranthema grandiflora,* hereinafter referred to by the cultivar name Carnival.

Carnival is a product of a planned breeding program which had the objective of creating new Chrysanthemum cultivars with freely breaking and vigorous growth habits, yellow novelty spoon tipped daisy flowers, and a nine week flowering response. Such traits in combination were not present or needed improvement in previously available commercial cultivars.

Carnival was originated from a hybridization made by applicant in a controlled breeding program in Parrish, Fla. in 1982. The female parent was designated PO-2314H-WS. The male parent of Carnival was Stripes, disclosed in U.S. Plant Pat. No. 4,544. Carnival was discovered and selected as one flowering plant within the progeny of the stated cross by applicant in November 1982 in a controlled environment in Parrish, Fla.

The first act of asexual reproduction of Carnival was accomplished when vegetative cuttings were taken from the initial selection in March 1983 in a controlled environment in Parrish, Fla. by a technician working under formulations established and supervised by applicant. Horticultural examination of selected units initiated in July 1983 has demonstrated that the combination of characteristics as herein disclosed for Carnival are firmly fixed and are retained through successive generations of asexual reproduction.

Carnival has not been observed under all possible environmental conditions. The phenotype may vary significantly with variations in environment such as temperature, light intensity, and day length. The following observations, measurements and comparisons describe plants grown in Parrish, Fla. under greenhouse conditions which approximate those generally used in commercial practice.

The following traits have been repeatedly observed and are determined to be basic characteristics of Carnival, which in combination distinguish this Chrysanthemum as a new and distinct cultivar:

1. Bright yellow quilled daisy with a spoon tip.
2. Performs well year around in pot mum programs.
3. Nine (9) week flower response.
4. Strong, vigorous, upright habit and excellent keeping quality.
5. Highly floriferous.
6. Average of 23 ray florets per capitulum.

7. Diameter across face of capitulum 8–9 cm.
8. Disc florets are yellow-green when immature, changing to golden yellow when mature.

Of the many commercial cultivars known to the present inventor, the most similar in comparison to Carnival is its paternal parent Stripes. In comparison to Stripes, Carnival has a one week slower flower response, lighter yellow ray floret flower color, performs better under northern winter conditions, and has a slightly smaller diameter of inflorescence.

The accompanying photographic drawing shows typical inflorescence and foliage characteristics of Carnival, with colors being as nearly true as possible with illustrations of this type. The photograph is in black and white, with several flowers being colored to accurately depict true flower color.

In the following description, color references are made to the Royal Horticultural Society Colour Chart. The color values were determined at approximately 4:00 p.m. on Sept. 26, 1986 under fluorescent lighting at Parrish, Fla.

Classification:

*Botanical.*—*Dendranthema grandiflora,* cv. Carnival.

*Commercial.*—Spoon tipped daisy pot.

INFLORESCENCE

A. Capitulum:
- *Form.*—Flat.
- *Type.*—Single.
- *Diameter across face.*—8–9 cm.

B. Corolla of ray florets:
- *Color (general tonality from a distance of three meters).*—Yellow.
- *Color (upper surface).*—5A.
- *Color (lower surface).*—5B.

C. Corolla of disc florets:
- *Color (mature).*—Yellow.
- *Color (immature).*—Yellow-green.

D. Reproductive organs:
- *Androecium.*—Present in disc florets only.
- *Gynoecium.*—Present in both disc and ray florets.

PLANT

A. General appearance:

*Height.*—20 cm above the top edge of the pot; height can vary depending upon growing conditions and cultural practices.

B. Foliage:

*Color* (*upper surface*).—147A.

*Color* (*lower surface*).—147B.

*Shape.*—Ovate, deeply lobed and serrate.

I claim:

1. A new and distinct cultivar of Chrysanthemum plant named Carnival, as illustrated and described, and parts thereof.

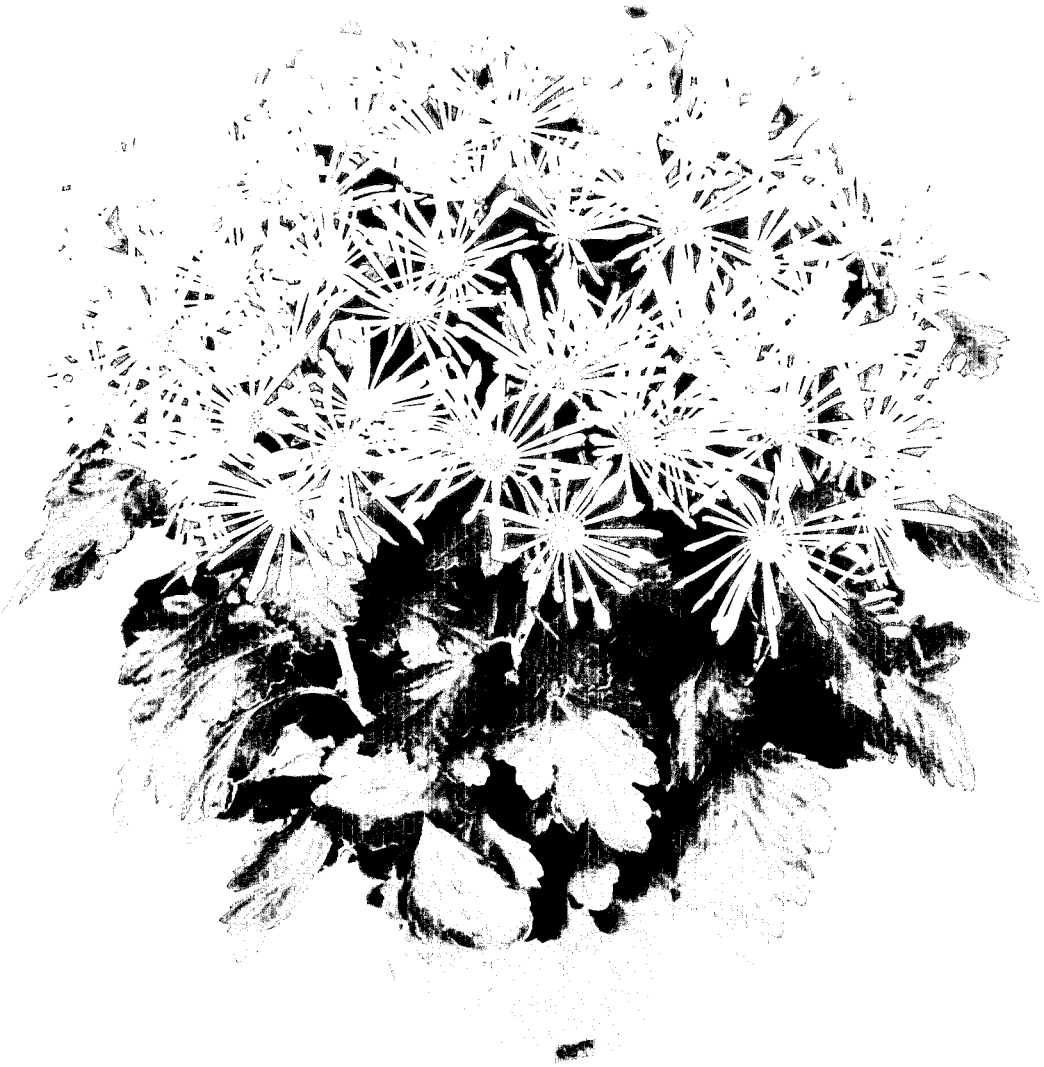

* * * * *